United States Patent [19]

Zinnes et al.

[11] 4,140,858

[45] Feb. 20, 1979

[54] 3-(1H-IMIDAZOL-1-YLMETHYL)-2-(DISUB-STITUTEDAMINOMETHYL)INDOLES AND A METHOD FOR THEIR PRODUCTION

[75] Inventors: Harold Zinnes, Rockaway; Neil A. Lindo, New Providence, both of N.J.

[73] Assignee: Warner-Lambert Company, Morris Plains, N.J.

[21] Appl. No.: 861,817

[22] Filed: Dec. 19, 1977

[51] Int. Cl.² ............................................ C07D 403/06
[52] U.S. Cl. ............................ 548/336; 260/326.12 R; 260/326.5 B; 260/326.85; 424/273 R; 424/274
[58] Field of Search ...................... 548/336; 424/273 R

[56] References Cited
U.S. PATENT DOCUMENTS

| 3,491,114 | 1/1970 | Suh et al. | 548/336 |
| 3,931,229 | 1/1976 | Zinnes et al. | 548/336 |

OTHER PUBLICATIONS

Andreani et al. J. Chem. Soc. (London) Part C, 1970, pp. 1157–1161.
Decodts et al. Chem. Abst. 1968, vol. 69, No. 96376a.

*Primary Examiner*—Natalie Trousof
*Attorney, Agent, or Firm*—David B. Ehrlinger; Stephen Raines; Frank S. Chow

[57] ABSTRACT

N,N-dialkyl-3-[(phenylthio)methyl]-1H-indole-2-methanamines or 3-(1H-imidazol-1-ylmethyl)-N,N,-dimethyl-1H-indole-2-methanamines and acid addition salts thereof which are useful pharmacological agents, especially antifungals, are disclosed. The compounds can be produced by reacting a thiophenols or imidazoles with the appropriate 2-alkyl-1,2,3,4-tetrahydropyrrolo[3,4-b]indole.

4 Claims, No Drawings

3-(1H-IMIDAZOL-1-YLMETHYL)-2-(DISUBSTITUTEDAMINOMETHYL)INDOLES AND A METHOD FOR THEIR PRODUCTION

SUMMARY AND DETAILED DESCRIPTION

The present invention relates to new 3-substituted-2-(dialkylaminomethyl)indoles. More particularly, the invention relates to new 2,3-di(disubstitutedaminomethyl)indoles of the formula

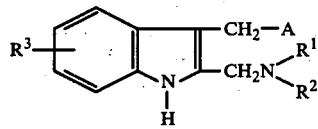

and acid addition salts thereof, and to a method for production of the foregoing compounds; where $R^1$ and $R^2$ are lower alkyl groups, $R^3$ is hydrogen, a lower alkyl group, halogen or a lower alkoxy group and A is phenylthio, lower alkylphenylthio, imidazol-1-yl or lower alkylimidazol-1-yl. The preferred compounds are those wherein $R^3$ is hydrogen, $R^1$ is methyl, $R^2$ is methyl or butyl and A is phenylthio or imidazol-1-yl.

The term "lower alkyl" is intended to mean an alkyl group of from one to six carbon atoms, such as methyl, ethyl, butyl, and isopentyl and the term "lower alkoxy" is intended to mean lower alkyl-O-. The term "acid addition salt" is intended to mean a salt such as the hydrochloride, sulfate, acetate, benzoate, citrate, hydrobromide, nitrate, etc. preferably the pharmaceutically acceptable salts such as the hydrochloride, sulfate, citrate, etc.

The term "halogen" is intended to mean chlorine, fluorine, iodine or bromine.

In accordance with the invention, the foregoing compounds of formula I can be prepared by reacting a compound of the formula

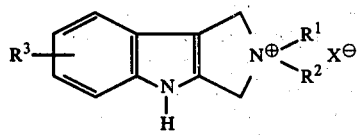

with a compound of the formulae

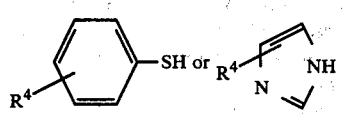

wherein $R^1$, $R^2$ and $R^3$ are as previously defined in formula I, X is lower alkylsulfate, bromine, chlorine or iodine, preferably iodine and $R^4$ is hydrogen or lower alkyl. When a thiophenol is used, a strong base such as sodium hydroxide or potassium hydroxide is added to the reaction mixture. While equamolar quantities of the reactants may be employed, an excess of the thiophenol or imidazole compound is generally preferred. This reaction may be carried out in a polar solvent such as an alcohol, water or mixtures thereof at temperatures of from about 50° C. to the reflux temperature of the solvent for periods of from fifteen minutes up to two days. The reaction is preferably conducted in water at reflux for a period of about four hours. The addition of an acid, such as hydrochloric acid converts the above formed free base to its acid addition salt.

Compounds of the formula II are prepared by reacting a compound of the formula

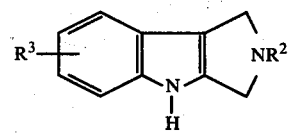

with a compound of the formula $$R^1X \qquad\qquad IV$$

wherein $R^1$, $R^2$ and $R^3$ are as previously defined. The reaction is conducted in a polar solvent. When employing an alkyl iodide, a rapid reaction takes place at room temperature in an acetone solvent; however, using alkyl chlorides and bromides usually requires higher reaction temperatures utilizing pressure vessels and reaction times of up to twenty-four hours.

Compounds of the formula III are prepared by reducing a compound of the formula

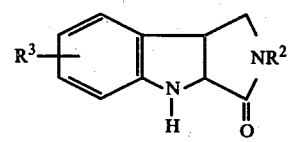

according to procedures reported in the Journal of Organic Chemistry 25(1960)1133 which is incorporated by reference.

The compounds of the invention are new chemical compounds of value as antifungal agents. More specifically, the compounds are active against Candida albicans and Trichophyton mentagrophytes. Activity is determined utilizing standard tube dilution tests in the absence of serum.

The invention is further illustrated by the following examples.

EXAMPLE 1

N,N-dimethyl-3-[(phenylthio)methyl]-1H-indole-2-methanamine

2-Methyl-1,2,3,4-tetrahydropyrrolo[3,4-b]indole methiodide, 7.9 g. is dissolved in 600 ml. hot water and treated with decolorizing carbon. The colorless filtrate is then stirred magnetically while thiophenol, 3.1 g., and sodium hydroxide, 1.2 g., are added. The mixture is refluxed three hours, cooled, and extracted with methylene chloride. The combined extracts, on drying and concentration, yield 6.4 g. of an oil which soon becomes a crystalline mass. Recrystallization from methanol gives 5.3 g. of the above named product, m.p. 92°–5° C. The addition of etherial hydrogen chloride to an alcoholic solution of the above compound gives the corresponding hydrochloride salt.

EXAMPLE 2

N-n-butyl-N-methyl-3-[(4'-ethylphenylthio)methyl]-1H-indole-2-methanamine

The above named compound is obtained by utilizing the procedure of Example 1 after substituting in the place of 2-methyl-1,2,3,4-tetrahydropyrrolo[3,4-b]indole methiodide, the following compound; 2-n-butyl-1,2,3,4-tetrahydropyrrolo[3,4-b]indole methiodide and in place of thiophenol the following compound; 4-ethylthiophenol.

EXAMPLE 3

3-(1H-imidazol-1-ylmethyl)-N,N-dimethyl-1H-indole-2-methanamine

2-Methyl-1,2,3,4-tetrahydropyrrolo[3,4-b]indole methiodide, 8.2 g., is dissolved in 500 ml. of hot water, and decolorized with charcoal. Imidazole, 10.2 g., is added, and the solution then refluxed for 43 hours. On cooling, an oil precipitates and is extracted from the reaction mixture using ether. The combined ether extracts are washed with water and sodium chloride solution, dried and concentrated to give 5.9 g. of crude product. Two recrystallizations from acetonitrile yields an analytical sample, m.p. 153°–155.5° C.

EXAMPLE 4

3-(1H-imidazol-1-ylmethyl)-N-n-butyl-N-methyl-1H-indole-2-methanamine

The above named compound is obtained by utilizing the procedure of Example 3 after substituting in the place of 2-methyl-1,2,3,4-tetrahydropyrrolo[3,4-b]indole methiodide, the following compound 2-n-butyl-1,2,3,4-tetrahydropyrrolo[3,4-b]-indole methiodide.

The hydrochloride salt of the above named compound is obtained by dissolving said compound in isopropanol and adding to it an ether solution of hydrogen chloride.

STARTING MATERIALS a. 2-methyl-1,2,3,4-tetrahydropyrrolo[3,4-b]indole methiodide.

Methyl iodide, 37 ml., is added in a single portion to a warm, vigorously stirred solution of 2-methyl-1,2,3,4-tetrahydropyrrolo[3,4-b]indole, 51.6 g., in dry acetone, 700 ml. A heavy crystalline precipitate of the title compound starts to separate almost immediately, and after 15 minutes of stirring is collected and washed thoroughly with additional acetone, giving 80–85 g. The product is essentially pure, and can be used directly.

b. 2-methyl-1,2,3,4-tetrahydropyrrolo[3,4-b]indole.

2-Methyl-1,4-dihydropyrrolo[3,4-b]indol-3(2H)-one, 1.7 g., and LiAlH$_4$, 2.3 g., are heated in refluxing dioxane, 300 ml., for five hours. The mixture is cooled and carefully hydrolyzed with excess water. Solids are filtered away and washed with dioxane, after which the filtrate is concentrated to dryness giving 1.4 g. of a crude brown product, m.p. 110°–120° C. Since the crude product is sensitive to air oxidation (darkens rapidly on standing), it is not further purified before methiodide preparation.

c. 2-methyl-1,4-dihydropyrrolo[3,4-b]indol-3(2H)-one.

1-Methyl-4-carbomethoxy-2,3-dioxopyrrolidine, 8.5 g., is heated on the steam bath for about 45 minutes to one hour in 150 ml. of a twenty percent aqueous hydrochloric acid solution. The resulting solution is cooled to room temperature and filtered. Sodium acetate is next added to neutralize the mixture of a pH of 4 to 5. Water is added as necessary to keep most of the solids in solution. Phenylhydrazine, 5.9 g., is then washed into the solution with a little methanol. A solid material precipitates immediately and is collected and washed with water. This crude phenylhydrazone is taken up in 100 ml. warm acetic acid and treated with 30 ml. concentrate hydrochloric acid. A vigorous reaction ensued after which the mixture is refluxed for 10 minutes. Cooling precipitates crude title compound, 16.7 g., m.p. about 300° (dec.). Recrystallization from a large volume of methanol raised the m.p. to 303°-6° (dec.).

d. 2-n-butyl-1,2,3,4-tetrahydropyrrolo[3,4-b]indole methiodide.

A slurry of 4.3 g. of 2-n-butyl-1,2,3,4-tetrahydropyrrolo[3,4-b]indole in dimethylformamide, 30 ml., is treated with methyl iodide, 4.3 g. After thirty minutes excess methyl iodide is removed using reduced pressure.

e. 2-n-butyl-1,2,3,4-tetrahydropyrrolo[3,4-b]indole.

2-n-Butyl-1,4-dihydropyrrolo[3,4-b]indol-3(2H)-one, 20 g., in dry tetrahydrofuran, 400 ml., is added slowly to a slurry of LiAl H$_4$, 14 g., in tetrahydrofuran, 250 ml. After refluxing twenty hours, the reaction mixture is hydrolyzed with 30 ml. of water, and filtered. After the solvent is removed, one obtains 20.1 g. of a reddish-brown solid. Recrystallization from methanol, 200 ml., gives 11 g. of the title compound, m.p. 151°-2°.

f. 2-n-butyl-1,4-dihydropyrrolo[3,4-b]indol-3(2H)-one.

1-n-Butyl-4-carbomethoxy-2,3-dioxopyrrolidine, 107 g., [Southwick and Owellen, J. Org. Chem. 25(1960)1133] is heated to boiling in a mixture of 600 ml. of a twenty percent aqueous hydrochloric acid solution and about 100 ml. of ninty-five percent ethanol. Solids dissolved in about ten minutes to give a yellow solution. After one hour of heating, the flask is cooled to about room temperature. Sodium acetate is then added to neutralize the reaction mixture to a pH of 4–5. In addition about 500 ml. of water is added during the neutralization to insure that most materials will remain in solution. Phenylhydrazine, 54 g., is then washed into the stirred mixture with methanol, 20 ml. The phenyl hydrazone starts to separate immediately, and is collected after 10 minutes of cooling and stirring. The material is dissolved in 200 ml. of acetic acid at 65° and treated with 100 ml. of concentrated hydrochloric acid. A strong exotherm takes the temperature up to about 110° which causes vigorous refluxing. Filtration of the cooled slurry yields 78 g. of the title compound, m.p. 215°–218° sinters at 210°. Dilution of the filtrate with water gives additional product, 7 g., m.p. after recrystallization from methanol: 216°–218°.

We claim:
1. A compound of the formula

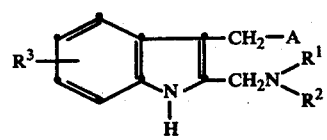

and pharmaceutically acceptable acid addition salts thereof, wherein $R^1$ and $R^2$ are lower alkyl, $R^3$ is hydrogen, lower alkyl, halogen or lower alkoxy and A is imidazol-1-yl or lower alkylimidazol-1-yl.

2. The compound of claim 1 having the name 3-(1H-imidazol-1-ylmethyl)-N,N-dimethyl-1H-indole-2-methanamine, and acid addition salts thereof.

3. The compound of claim 1 having the name 3-(1H-imidazol-1-ylmethyl)-N-n-butyl-N-methyl-1H-indole-2-methanamine, and acid addition salts thereof.

4. A process for the preparation of a compound of the formula

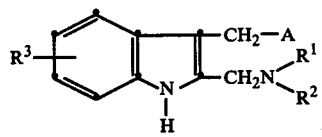

and acid addition salts thereof, which comprises reacting a compound of the formula

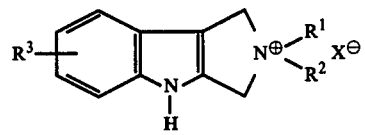

with a compound of the formulae

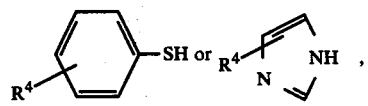

with the proviso that when said thiophenols are employed an equivalent amount of a strong base is added, wherein $R^1$, $R^2$ and $R^3$ are as defined in claim 1, X is lower alkylsulfate, bromine, chlorine or iodine and $R^4$ is hydrogen or lower alkyl and the product is isolated as the free base or an acid addition salt thereof.

* * * * *